(12) United States Patent
Gimi et al.

(10) Patent No.: US 6,878,828 B2
(45) Date of Patent: Apr. 12, 2005

(54) SYNTHESIS OF 2-ALKYLCYSTEINE VIA SUBSTITUTED THIAZOLINE ESTER

(75) Inventors: Rayomand H. Gimi, Chelmsford, MA (US); Mukund S. Chorghade, Natick, MA (US); Sunil V. Mhaskar, Natick, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 10/439,282

(22) Filed: May 15, 2003

(65) Prior Publication Data

US 2003/0236435 A1 Dec. 25, 2003

Related U.S. Application Data

(60) Provisional application No. 60/381,012, filed on May 15, 2002, provisional application No. 60/381,021, filed on May 15, 2002, provisional application No. 60/380,894, filed on May 15, 2002, provisional application No. 60/380,910, filed on May 15, 2002, provisional application No. 60/380,880, filed on May 15, 2002, provisional application No. 60/381,017, filed on May 15, 2002, provisional application No. 60/380,895, filed on May 15, 2002, provisional application No. 60/380,903, filed on May 15, 2002, provisional application No. 60/381,013, filed on May 15, 2002, provisional application No. 60/380,878, filed on May 15, 2002, provisional application No. 60/380,909, filed on May 15, 2002, and provisional application No. 60/392,833, filed on Jun. 27, 2002.

(51) Int. Cl.$^7$ ............................................. C07D 277/04
(52) U.S. Cl. ....................... 548/201; 548/146; 562/553; 562/536
(58) Field of Search ................................. 562/553, 556, 562/561, 575; 548/146, 200, 201

(56) References Cited

U.S. PATENT DOCUMENTS

| | | | |
|---|---|---|---|
| 4,406,905 A | 9/1983 | Zähner et al. | |
| 5,554,753 A | 9/1996 | O'Donnell et al. | |
| 5,840,739 A | 11/1998 | Bergeron, Jr. | |
| 5,872,259 A | 2/1999 | Reuter | |
| 5,929,232 A | 7/1999 | Jacobsen et al. | |
| 6,083,966 A | 7/2000 | Bergeron, Jr. | |
| 6,159,983 A | 12/2000 | Bergeron, Jr. | |
| 6,383,233 B1 | 5/2002 | Reuter | |
| 6,428,583 B1 | 8/2002 | Reuter | |
| 6,521,652 B1 | 2/2003 | Bergeron | |
| 6,525,080 B1 | 2/2003 | Bergeron | |
| 6,559,315 B1 | 5/2003 | Bergeron | |
| 2003/0088105 A1 * | 5/2003 | Krich et al. | ................. 546/167 |
| 2003/0220504 A1 | 11/2003 | Chorghade et al. | |
| 2003/0225287 A1 | 12/2003 | Chorghade et al. | |
| 2003/0229231 A1 | 12/2003 | Chorghade et al. | |
| 2003/0236404 A1 | 12/2003 | Gimi et al. | |
| 2003/0236426 A1 | 12/2003 | Chorghade et al. | |
| 2003/0236434 A1 | 12/2003 | Gimi et al. | |
| 2004/0002613 A1 | 1/2004 | Chorghade et al. | |
| 2004/0006224 A1 | 1/2004 | Chorghade et al. | |
| 2004/0024224 A1 | 2/2004 | Chorghade et al. | |

FOREIGN PATENT DOCUMENTS

| | | |
|---|---|---|
| DE | 20 20 866 | 11/1971 |
| DE | 30 02 989 A1 | 7/1981 |
| EP | 1 302 467 A2 | 4/2003 |
| WO | 1 292 170 | 10/1972 |
| WO | WO 94/11367 | 5/1994 |
| WO | WO 97/36885 | 10/1997 |
| WO | WO 00/01670 | 1/2000 |
| WO | WO 00/12493 A1 | 3/2000 |
| WO | WO 00/16763 | 3/2000 |

OTHER PUBLICATIONS

Ino et al., Total Synthesis of the Antimycoplasma Antibiotic Micacocidin, Tetrahedron letters 1998 39(21) 3509–3512.*

Ehrler, Juerg, and Farooq, Saleem, "Total Synthesis of Thiangazole," *Synlett*, 702–704 (1994).

Kishore, V., et al., "Synthesis of α–Poly–[N$^\epsilon$–(2–aryl–Δ$^2$–thiazoline–4–carbonyl)–L–lysines] With Antiviral Activity," *Indian Journal of Chemistry 15B*: 255–257 (1977).

Zamri, Adel, and Abdallah, Mohamed A., "An Improved Stereocontrolled Synthesis of Pyochelin, Siderophore of *Pseudomonas aeruginosa* and *Burkholderia cepacia*," *Tetrahedron 56*: 249–256 (2000).

Bergeron, R., et al., "Desazademethyldesferrithiocin Analogues as Orally Effective Iron Chelators," *J. Med. Chem.*, 42:95–108 (1999).

Bergeron, R. et al., "The Desferrithiocin Pharmacophore," *J. Med. Chem.*, 37:1411–1417 (1994).

Bergeron, R. et al., "Effects of C–4 Stereochemistry and C–4 Hydroxylation on the Iron Clearing Efficiency and Toxicity of Desferrithiocin Analogues," *J. Med. Chem.*, 42:2432–2440 (1999).

(Continued)

Primary Examiner—Johann Richter
Assistant Examiner—Karl Puttlitz
(74) Attorney, Agent, or Firm—Hamilton, Brook, Smith & Reynolds, P.C.

(57) ABSTRACT

Non-natural amino acids such as 2-alkylated amino acids allow for the synthesis of a wider variety of peptidal and non-peptidal pharmaceutically active agents. In one embodiment, the present invention relates to a method of preparing a 2-alkylcysteine comprising condensing cysteine with an aryl nitrile to form a 2-arylthiazoline-4-carboxylic acid, esterifying the 2-arylthiazoline-4-carboxylic acid using a substituted or unsubstituted alcohol group comprising one or more chiral carbons, and alkylating at the 4-position of the thiazoline ring to form a 2-aryl-4-alkyl-thiazoline-4-carboxylic acid ester. The chiral templates present in the thiazoline carboxylic acid ester can provide face selectivity, and consequently desired stereochemistry, during the delivery of an alkyl group to the 4-position of the thiazoline ring. The present invention also discloses a method of preparing a class of iron chelating agents related to desferrithiocin, all of which contain a thiazoline ring. In one embodiment, an aryl nitrile is condensed with cysteine or a 2-alkyl cysteine.

13 Claims, No Drawings

OTHER PUBLICATIONS

Bergeron, R. et al., "Synthesis and Biological Evaluation of Naphthyldesferrithiocin Iron Chelators," *J. Med. Chem.*, 39:1575–1581 (1996).

Bergeron, R. et al., "Evaluation of Desferrithiocin and Its Synthetic Analogues as Orally Effective Iron Chelators," *J. Med. Chem.*, 34:2072–2078 (1991).

Bergeron, R. et al., "Evaluation of the Desferrithiocin Pharmacophore as a Vector for Hydroxamates," *J. Med. Chem.*, 42:2881–2886 (1999).

Bergeron, R. et al., "An Investigation of Desferrithiocin Metabolism," *J. Med. Chem.*, 37:2889–2895 (1994).

Bergeron, R. et al., "A Comparative Study of the Iron–Clearing Properties of Desferrithiocin Analogues with Desferrioxamine B in a *Cebus* Monkey Model," *Blood*, 81(8):2166–2173 (1993).

Bergeron, R. et al., "Pharmacokinetics of Orally Administered Desferrithiocin Analogs in *Cebus Apella* Primates," *Drug Metabolism and Disposition*, 27(12):1496–1498 (1999).

Mulqueen, G. C., et al., "Synthesis of the Thiazoline–based Siderophore (S)–Desferrithiocin," *Tetrahedron*, 49(24):5359–5364 (1993).

O'Donnell, M. J., et al., "α–Methyl Amino Acids by Catalytic Phase–Transfer Aklylations," *Tetrahedron Letters*, 23(41):4259–4262 (1982).

U.S. Appl. No. 10/439,263, Mukund S. Chorghade, Rayomand H. Gimi, Peter McDonnell and Paul Wolstenholme-Hogg, filed May 15, 2003.

* cited by examiner

SYNTHESIS OF 2-ALKYLCYSTEINE VIA SUBSTITUTED THIAZOLINE ESTER

RELATED APPLICATIONS

This application claims the benefit of U.S. Provisional Application Nos. 60/381,012, 60/381,021, 60/380,894, 60/380,910, 60/380,880, 60/381,017, 60/380,895, 60/380,903, 60/381,013, 60/380,878 and 60/380,909, all of which were filed May 15, 2002. This application also claims the benefit of U.S. Provisional Application No. 60/392,833, filed Jun. 27, 2002. The entire teachings of the above-referenced applications are incorporated herein by reference.

BACKGROUND OF THE INVENTION

Alpha-amino acids are useful starting materials in the synthesis of peptides, as well as non-peptidal, pharmaceutically active peptidomimetic agents. In order to enable the synthesis of a large number of compounds from an amino acid precursor, it is advantageous to have naturally occurring and non-naturally occurring amino acids. Non-naturally occurring amino acids typically differ from natural amino acids by their stereochemistry (e.g., enantiomers), by the addition of alkyl groups or other functionalities, or both. At this time, the enantiomers of naturally occurring amino acids are much more expensive than the naturally occurring amino acids. In addition, there are only a limited number of commercially available amino acids that are functionalized or alkylated at the alpha-carbon, and often syntheses involve the use of pyrophoric or otherwise hazardous reagents. Moreover, the syntheses are often difficult to scale up to a commercially useful quantity. Consequently, there is a need for new methodologies of producing such non-naturally occurring amino acids.

Non-naturally occurring amino acids of interest include the (R)- and (S)-isomers of 2-methylcysteine, which are used in the design of pharmaceutically active moieties. Several natural products derived from these isomers have been discovered in the past few years. These natural products include desferrithiocin, from *Streptomyces antibioticus*; as well as tantazole A, mirabazole C, and thiangazole, all from blue-green algae. These compounds have diverse biological activities ranging from iron chelation to murine solid tumor-selective cytotoxicity to inhibition of HIV-1 infection.

Desferrithiocin, deferiprone, and related compounds represent an advance in iron chelation therapy for subjects suffering from iron overload diseases. Present therapeutic agents such as desferroxamine require parenteral administration and have a very short half-life in the body, so that patient compliance and treatment cost are serious problems for subjects receiving long-term chelation therapy. Desferrithiocin and related compounds are effective when orally administered, thereby reducing patient compliance issues. Unfortunately, (S)-2-methylcysteine, which is a precursor to the more active forms of desferrithiocin and related compounds, remains a synthetic challenge. Therefore, there is a need for novel methods of producing 2-methylcysteine at a reasonable cost, and means of isolating the desired enantiomer.

SUMMARY OF THE INVENTION

A useful and efficient method of preparing 2-alkylcysteine involves condensing cysteine with an aryl nitrile to form a 2-arylthiazoline-4-carboxylic acid, esterifying the 2-arylthiazoline-4-carboxylic acid using a substituted or unsubstituted alcohol group comprising one or more chiral carbons, and alkylating at the 4-position of the thiazoline ring to form a 2-aryl-4-alkyl-thiazoline-4-carboxylic acid ester. Esterifying a carboxylic acid with a chiral alcohol results in the formation of a chiral template. The chiral templates present in the thiazoline carboxylic acid ester can provide face selectivity, and consequently stereochemical control, during the delivery of an alkyl group to the 4-position of the thiazoline ring. The chiral templates present in the thiazoline carboxylic acid ester produces an enantiomeric excess of one isomer.

In one aspect, the present invention relates to a method of preparing an optically active 2-alkylated cysteine represented by Structural Formula (I):

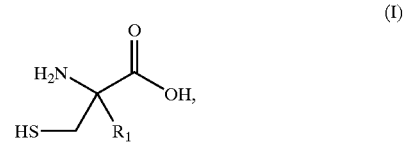

or a salt thereof, wherein $R_1$ is a substituted or unsubstituted alkyl group, the method comprising:

(a) coupling a compound (which may be an (R) or (S)-isomer or a mixture thereof) represented by Structural Formula (II):

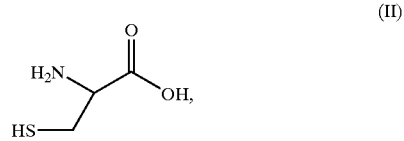

or a salt thereof, with a substituted or unsubstituted aryl nitrile of the formula Ar—CN, wherein Ar is a substituted or unsubstituted aryl group; thereby forming a substituted thiazoline carboxylic acid represented by Structural Formula (III):

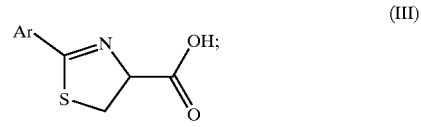

(b) esterifying the substituted thiazoline carboxylic acid with R*—OH, wherein R* is a substituted or unsubstituted alkyl group comprising one or more chiral carbon atoms; thereby forming a substituted thiazoline carboxylic acid ester represented by Structural Formula (IV):

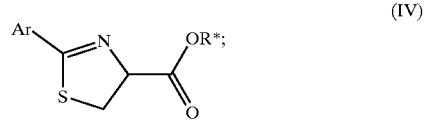

(c) alkylating the substituted thiazoline carboxylic acid ester with one or more bases and $R_1X$, wherein X is a leaving group and $R_1$ is as defined above; thereby forming an alkylated substituted thiazoline carboxylic acid ester represented by Structural Formula (V):

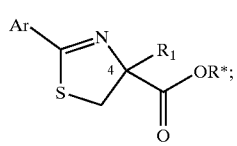
(V)

(d) hydrolyzing the alkylated substituted thiazoline carboxylic acid ester with base or acid, thereby forming an alkylated substituted thiazoline carboxylic acid represented by Structural Formula (VI):

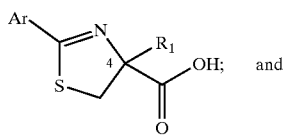
(VI)

and (e) reacting the alkylated substituted thiazoline carboxylic acid with acid (preferably an inorganic acid such as HCl, HBr or sulfuric acid), thereby forming the 2-alkylated cysteine represented by Structural Formula (I).

The methods described above may additionally comprise the step of purifying or ultrapurifying the alkylated substituted thiazoline carboxylic acid or the alkylated substituted thiazoline carboxylic acid ester. Purifying the ester or the acid can comprise further resolving the enantiomers or diasteromers of the alkylated substituted thiazoline carboxylic acid or the alkylated substituted thiazoline carboxylic acid ester. Additionally, the methods can comprise the isolation of the enantiomers of the synthesis products. Preferably, the (S)-enantiomer of 2-alkyleysteine is isolated (or the corresponding 4-alkyl-2-arylthiazoline carboxylic acid or salt or ester thereof), for example, (S)-2-methylcysteine.

In another aspect, the present invention relates to a method of preparing a compound represented by Structural Formula (VII):

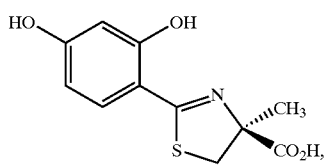
(VII)

or a salt thereof, the method comprising:

(a) coupling a compound (which may be an (R) or (S)-isomer or a mixture thereof) represented by Structural Formula (VIII):

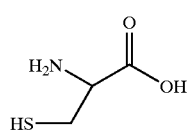
(VIII)

or a salt thereof, with a substituted or unsubstituted aryl nitrile of the formula Ar—CN, wherein Ar is a substituted or unsubstituted aryl group; thereby forming a substituted thiazoline carboxylic acid represented by Structural Formula (IX):

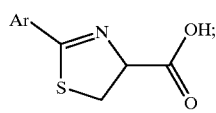
(IX)

(b) esterifying the substituted thiazoline carboxylic acid with R*—OH, wherein R* is a substituted or unsubstituted alkyl group comprising one or more chiral carbon atoms; thereby forming a substituted thiazoline carboxylic acid ester represented by Structural Formula (X):

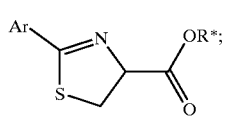
(X)

(c) alkylating the substituted thiazoline carboxylic acid ester with one or more bases and $CH_3X$, wherein X is a leaving group; thereby forming an alkylated substituted thiazoline carboxylic acid ester represented by Structural Formula (XI):

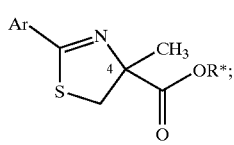
(XI)

(d) hydrolyzing the alkylated substituted thiazoline carboxylic acid ester with base or acid, thereby forming an alkylated substituted thiazoline carboxylic acid represented by Structural Formula (XII):

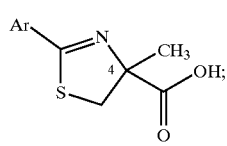
(XII)

(e) optionally, purifying the (S)-isomer of the alkylated substituted thiazoline carboxylic acid;

(f) reacting the (S)-isomer of the alkylated substituted thiazoline carboxylic acid with acid, thereby forming (S)-2-methylcysteine; and (g) coupling (S)-2-methylcysteine with 2,4-dihydroxybenzonitrile, thereby forming the compound represented by Structural Formula (VII).

Advantages of the present invention include the facile synthesis of a 2-alkyl cysteine from cysteine, an inexpensive and readily available starting material. 2-Methylcysteine prepared by the method of the present invention can be coupled to 2,4-dihydroxybenzonitrile to form 4'-hydroxydesazadesferrithiocin, or 4,5-dihydro-2-(2,4-dihydroxyphenyl)-4-methylthiazole-4(S)-carboxylic acid, an iron chelating agent.

DETAILED DESCRIPTION OF THE INVENTION

A useful and efficient method of preparing 2-alkylcysteine involves condensing cysteine with an aryl nitrile to form a 2-arylthiazoline-4-carboxylic acid, esterifying the 2-arylthiazoline-4-carboxylic acid using a substituted or unsubstituted alcohol group comprising one or more chiral carbons, and alkylating at the 4-position of the thiazoline ring to form a 2-aryl-4-alkyl-thiazoline-4-carboxylic acid ester. The chiral templates present in the thiazoline carboxylic acid ester can provide face selectivity, and consequently desired stereochemistry, during the delivery of an alkyl group to the 4-position of the thiazoline ring. The resulting enantiomers of the product can be further purified and isolated into pure or substantially pure enantiomer components by a number of methods.

The condensation of an aryl nitrile and cysteine typically occurs in a polar, protic solvent in the presence of an excess of base. Typically, the aryl nitrile and cysteine are refluxed together for several hours, such as 1–20 hours, 2–15 hours, 4–10 hours, or 6–8 hours. Refluxing preferably occurs in an inert atmosphere, such as nitrogen or argon. Preferred aryl nitrites include aryl nitrites where the aryl group is a substituted or unsubstituted phenyl group. Unsubstituted phenyl and substituted phenyl containing such groups as —OH or alkyl are preferred. Suitable polar, protic solvents include, but are not limited to, water, methanol, ethanol, formic acid, acetic acid, dimethylformamide, N-ethylacetamide, formaldehyde diethyl acetal, and long chain alcohols (e.g., propanol and isopropanol). An alcohol, such as methanol or ethanol, is a preferred solvent. Suitable bases include secondary and tertiary amines such as dimethylamine, diethylamine, trimethylamine, triethylamine, diisopropylamine, and diisopropylethylamine. The base can be added in excess, such as one or more equivalents relative to the amount of cysteine. Suitable amounts of base have at least about one equivalent of base, and range from about 1 to about 10, about 1 to about 5, about 1 to about 3, and about 1 to about 2 equivalents, relative to the amount of cysteine. In one example, cysteine, benzonitrile, and 5 equivalents of triethylamine are refluxed in ethanol for about 6–8 hours to obtain a 2-phenylthiazoline-4-carboxylic acid.

Alternatively, an aryl imidate (e.g., a benzimidate, where the benzene ring can have one or more substituents, as described below) can be condensed with cysteine to form a substituted thiazoline carboxylic acid. The substituted thiazoline carboxylic acid can be formed by coupling an aryl imidate, such as benzimidate, with a cysteine, such as the cysteine represented by Structural Formula (II). Typically, coupling of a cysteine or a 2-alkylcysteine with an aryl imidate includes reacting a cysteine (or a related compound) with the aryl imidate under basic conditions. Acceptable bases include trimethylamine; triethylamine; dimethylamine; diethylamine; diphenylamine; diisopropylamine; diisopropylethylamine; 1,4-diazabicyclo[2.2.2]octane (DABCO); 1,5-diazabicyclo-[4.3.0]-non-5-ene (DBN); and the like.

Aryl imidates can be prepared, for example, for aryl nitriles, aryl carboxylic acids, and aryl amides. Methods of forming aryl imidates are discussed in co-filed U.S. Patent Application Ser. No. 60/380,909, filed May 15, 2002, the entire contents of which are incorporated herein by reference. In one example, an aryl carboxylic acid (e.g., benzoic acid) is converted into an acid chloride, then an amide, followed by reaction with a trialkyloxonium hexafluorophosphate or a trialkyloxonium tetrafluoroborate to form the aryl imidate. In a second example, an aryl nitrile is converted into an aryl imidate through reaction with an alcohol in the presence of an acid, as is described below.

An ester of a carboxylic acid can be produced using, for example, an alcohol. In one embodiment of the present invention, a substituted thiazoline carboxylic acid ester represented by Structural Formula (IV) is formed with a chiral alcohol represented by R*—OH wherein R* is a substituted or unsubstituted alkyl group comprising one or more chiral carbon atoms. Preferably, R* is a primary or secondary substituted or unsubstituted alkyl group. More preferably, R* is a substituted or unsubstituted cyclic or polycyclic (e.g., bicyclic tricyclic) alkyl group. Preferably, the chiral alcohol used is substantially optically pure (1R, 2R,3R,5S)-(−)-isopinocamphenol or (1S,2R,5R)-(+)-isomenthol. The substituted thiazoline carboxylic acid ester may be formed through various means. In one embodiment, a substituted thiazoline carboxylic acid ester is produced through the acid catalyzed reaction of a substituted thiazoline carboxylic acid with a chiral alcohol. Common acid catalysts include sulfuric acid and p-toluenesulfonic acid. A substituted thiazoline carboxylic acid ester can also be produced via intermediate reactive acid derivatives such as acid chlorides. Alternatively, a substituted thiazoline carboxylic acid is treated with a chiral alcohol in the presence of a coupling agent. Coupling agents include, but are not limited to dicyclohexylcarbodiimide (DCC); alkyl chloroformate and triethylamine; pyridinium salts and tributylamine; Amberlyst-15; phenyl dichlorophosphate; diethyl azodicarboxylate and triphenyl phosphine; DCC and an aminopyridine; 2-chloro-1,3,5-trinitrobenzene and pyridine; 1,1'-carbonylbis(3-methylimidazolium) triflate; di-2-pyridyl carbonate, polystyryl diphenylphosphine; (trimethylsilyl) ethoxyacetylene; chlorosulfonyl isocyanate; chlorosilanes, $MeSO_2Cl-Et_3N$; $Ph_3P-CCL_4-Et_3N$; and N,N'-carbonyldiimidazole. Preferably, dicyclohexylcarbodiimide (DCC) is the coupling agent. As an example, a substituted thiazoline carboxylic acid may be treated with a chiral alcohol, DCC, and 4-(dimethylamino)pyridine (DMAP) in tetrahydrofuran (THF) at room temperature or higher to form a substituted thiazoline carboxylic acid ester.

The 2-arylthiazoline-4-carboxylic acid ester can be alkylated in the presence of one or more bases, an alkylating agent, and optionally a phase transfer catalyst. Typically, the 2-arylthiazoline-4 carboxylic acid ester is reacted with one or more equivalents (e.g., about 1 to 10, about 1 to 5, about 1 to 3, or about 1.5 to 2.5 equivalents) of base and one or more equivalents (e.g., about 1 to 5, about 1 to 2, about 1 to 1.5, or about 1 to 1.1 equivalents) of an alkylating agent in a polar, aprotic solvent at about −80 to 40° C., about −50 to 25° C., about −20 to 10° C., or about −5 to 5° C.

Alkylating agents are of the formula $R_1X$, where $R_1$ and X are as defined above. Preferred $R_1$ groups include substituted or unsubstituted C1–C4 alkyl groups, for example, methyl or benzyl. The leaving group X is typically a weak base. Suitable leaving groups include halogen, tosyl, mesyl, triflyl, brosyl, p-nitrophenyl, and 2,4-dinitrophenyl groups. Halogens include bromine, chlorine, and iodine. Iodine is a preferred leaving group. Preferred bases include potassium t-butoxide, sodium methoxide, sodium ethoxide, and sodium amide. Suitable polar, aprotic solvents include, but are not limited to, dimethylformamide, dimethyl sulfoxide, acetonitrile, acetone, tetrahydrofuran (THF), and hexamethylphosphoramide. Tetrahydrofuran (THF) is a preferred solvent.

In one example, a 2-phenylthiazoline-4 carboxylic acid ester (e.g., the ethyl, methyl, t-butyl, or isopropyl ester) is reacted with about 2 equivalents of base and about 1 equivalent of methyl iodide in tetrahydrofuran (THF) at 0° C. to form a C4 position n-alkylated 2-phenyl-4-carboxylic acid ester (e.g., the ethyl, methyl, t-butyl, or isopropyl ester).

Alternatively, the 2-arylthiazoline-4-carboxylic acid ester can be alkylated in the presence of a phase transfer catalyst.

Examples of phase transfer catalysts include benzyl triethyl ammonium chloride, benzyl trimethyl ammonium chloride, benzyl tributyl ammonium chloride, tetrabutyl ammonium bromide, tetraethyl ammonium bromide, tetrabutyl ammonium hydrogen sulfate, tetramethyl ammonium iodide, tetramethyl ammonium chloride, triethylbutyl ammonium bromide, tributyl ethyl ammonium bromide, tributyl methyl ammonium chloride, 2-chloroethylamine chloride HCl, bis(2-chloroethyl)amine HCl, 2-dimethylaminoethyl chloride HCl, 2-ethylaminoethyl chloride HCl, 3-dimethylaminopropyl chloride HCl, methylamine HCl, dimethylamine HCl, trimethylamine HCl, monoethylamine HCl, diethylamine HCl, triethylamine HCl, ethanolamine HCl, diethanolamine HCl, triethanolamine HCl, cyclohexylamine HCl, dicyclohexylamine HCl, cyclohexylamine HCl, diisopropylethylamine HCl, ethylenediamine HCl, aniline HCl, methyl salicylate, ethyl salicylate, butyl salicylate amyl salicylate, isoamyl salicylate, 2-ethylsalicylate, and benzyl salicylate.

The 2-aryl-4-alkyl-thiazoline-4-carboxylic acid ester can be hydrolyzed with either base or acid to form a 2-aryl-4-alkyl-thiazoline-4-carboxylic acid. The 2-aryl-4-alkyl-thiazoline-4-carboxylic acid then can be reacted with acid to form a 2-alkylcysteine, such as 2-methylcysteine.

In some embodiments of the present invention, the products (e.g., compounds that have been alkylated), either enantiomers or diastereomers, of the above noted syntheses can be purified or ultrapurified. For example, the 2-aryl-4-alkyl-thiazoline-4-carboxylic acid ester can be further resolved into (R) and (S)-isomers based on the thiazoline 4-carbon. The 2-aryl-4-alkyl-thiazoline-4-carboxylic acid ester can be purified using the technique of emulsion crystallization. In one form the method includes further resolving the 2-aryl-4-alkyl-thiazoline-4-carboxylic acid ester into its (R) and (S)-isomers based on the thiazoline 4-carbon, isolating the (S)-isomer, and reacting the (S)-isomer with acid to form (S)-2-alkylcysteine. Alternatively, the 2-aryl-4-alkyl-thiazoline-4-carboxylic acid ester can be reacted with either base or acid to form a 2-aryl-4-alkyl-thiazoline-4-carboxylic acid and then the 2-aryl-4-alkyl-thiazoline-4-carboxylic acid can be further resolved into its (R) and (S)-isomers. The 2-aryl-4-alkyl-thiazoline-4-carboxylic acid can be further resolved, for example, using the technique of emulsion crystallization or by the formation of a diastereomeric salt. In one embodiment, the 2-aryl-4-alkyl-thiazoline-4-carboxylic acid is resolved into its (R) and (S)-isomers, the (S)-isomer is isolated, and the (S)-isomer is reacted with acid to form (S)-2-alkylcysteine. Alternatively, the 2-aryl-4-alkyl-thiazoline-4-carboxylic acid ester is reacted with acid to form 2-alkylcysteine, the 2-alkylcysteine is resolved into its (R) and (S)-isomers, and the (S)-isomer is isolated, producing (S)-2-alkylcysteine.

Chiral carboxylic acids can be purified through further resolution of enantiomers by forming a diastereomeric salt with the chiral carboxylic acid and a chiral amine. Suitable chiral amines include arylalkylamines such as 1-alkyl-1-aminoalkanes and 1-aryl-1-aminoalkanes. Examples include (R)-1-phenylethylamine, (S)-1-phenylethylamine, (R)-1-tolylethylamine, (S)-1-tolylethylamine, (R)-1-phenylpropylamine, (S)-1-propylamine, (R)-1-tolylpropylamine, and (S)-1-tolylpropylamine. Preferably, (R)-1-phenylethylamine [i.e., (R)-1-phenyl-1-aminoethane] is used to further resolve the chiral carboxylic acid mixture. Resolution of chiral compounds using diastereomeric salts is further described in *CRC Handbook of Optical Resolutions via Diastereomeric Salt Formation* by David Kozma (CRC Press, 2001), incorporated herein by reference in its entirety.

Chiral carboxylic acids and functionalized derivatives of chiral carboxylic acids, such as chiral carboxylic esters, can also be purified by emulsion crystallization, as described in U.S. Pat. Nos. 5,872,259, 6,383,233 and 6,428,583 issued to Reuter, the teachings of which are incorporated herein in their entirety by reference. Briefly, emulsion crystallization is a process for separating a desired substance from an aggregate mixture. The process involves forming a three phase system, the first phase comprising the aggregate mixture, the second phase being liquid and comprising a transport phase, and the third phase comprising a surface upon which the desired substance can crystallize. A chemical potential exists for crystal growth of the desired substance in the third phase of the system, thereby creating a flow of the desired substance from the first phase through the second phase to the third phase, where the desired substance crystallizes and whereby an equilibrium of the activities of the remaining substances in the aggregate mixture is maintained between the first phase and the second phase.

In one example of emulsion crystallization, a solution of the racemic mixture is supersaturated (by either cooling, adding a solvent in which one or more components are sparingly soluble or by evaporation of the solution). Ultrasonication eventually helps the process of forming an emulsion. The mixture is then seeded with crystals of the desired, optically active acid along with an additional quantity of surfactant and an anti-foaming agent. The desired product usually crystallizes out and can be separated by filtration.

Once the chiral carboxylic acids or chiral carboxylic acid esters have been further resolved, the desired isomer can be isolated. Typically, the (S)-isomer is isolated. For example, a (S)-2-alkylcysteine, a 2-aryl-4-alkyl-thiazoline-(S)-4-carboxylic acid, or a 2-aryl-4-alkyl-thiazoline-(S)-4-carboxylic acid ester is isolated. Preferably, a 2-aryl-4-alkyl-thiazoline-(S)-4-carboxylic acid or a 2-aryl-4-alkyl-thiazoline-(S)-4-carboxylic acid ester is isolated.

In a preferred embodiment, (S)-2-methylcysteine is formed and isolated. Cysteine or a 2-alkylcysteine such as (S)-2-methylcysteine can be coupled to a substituted or unsubstituted aryl nitrile such as a substituted or unsubstituted benzonitrile. Preferably, the substituents on benzonitrile will not interfere with the coupling reaction. In one form of the present invention, (S)-2-methylcysteine is coupled to 2,4-dihydroxybenzonitrile to form 4,5-dihydro-2-(2,4-dihydroxyphenyl)-4-methylthiazole-4(S)-carboxylic acid (also known as 4'-hydroxydesazadesferrithiocin). In yet another embodiment, (S)-2-methylcysteine is coupled to 2-hydroxybenzonitrile to form 4,5-dihydro-2-(2-hydroxyphenyl)-4-methylthiazole-4(S)-carboxylic acid (also known as desazadesferrithiocin).

Typically, coupling of cysteine or a 2-alkylcysteine and a substituted or unsubstituted benzonitrile includes converting the benzonitrile into a benzimidate. The benzimidate can be formed, for example, by reacting the benzonitrile with an alcohol such as methanol, ethanol, n-propanol, or isopropanol in the presence of an acid such as hydrochloric acid. The benzimidate is then reacted with the cysteine (or related compound) under basic conditions. Acceptable bases include trimethylamine, triethylamine, triphenylamine, and the like. The reaction between the benzimidate and the cysteine results in the thiazoline (or 4,5-dihydrothiazole) containing product. When forming the benzimidate from a hydroxylated benzonitrile (e.g., 2,4-dihydroxybenzonitrile), the hydroxyl groups are advantageously protected (e.g., with a substituted or unsubstituted alkyl or arylalkyl group such as a benzyl group). The protecting groups are subsequently cleaved, typically by catalytic hydrogenation.

Suitable benzonitriles and benzimidates for use in the above coupling reaction can be synthesized by methods described in co-pending U.S. Patent Application Nos. 60/381,013, 60/380,878 and 60/380,909, filed May 15, 2002. The entire contents of these applications are incorporated herein by reference.

The methods of the claimed invention can be used to manufacture other related desferrithiocin analogs and derivatives. Examples of such analogs include those described in U.S. Pat. Nos. 5,840,739, 6,083,966, 6,159,983, 6,521,652 and 6,525,080, both issued to Bergeron, the contents of which are incorporated herein by reference. Additional examples can be found in International Application Nos. PCT/US93/10936, published as WO 94/1137 on May 5, 1994; PCT/US97/04666, published as WO 97/36885 on Oct. 9, 1997; and PCT/US99/19691, published as WO 00/12493 on Mar. 9, 2000, the entire contents of which are incorporated herein by reference.

An alkyl group is a hydrocarbon in a molecule that is bonded to one other group in the molecule through a single covalent bond from one of its carbon atoms. Alkyl groups can be cyclic, branched or unbranched, and/or saturated or unsaturated. Typically, an alkyl group has one to about 24 carbons atoms, or one to about 12 carbon atoms. Lower alkyl groups have one to four carbon atoms and include methyl, ethyl, n-propyl, iso-propyl, n-butyl, sec-butyl and tert-butyl.

Aromatic (or aryl) groups include carbocyclic aromatic groups such as phenyl, p-tolyl, 1-naphthyl, 2-naphthyl, 1-anthracyl and 2-anthracyl. Aromatic groups also include heteroaromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl.

Aromatic groups also include fused polycyclic aromatic ring systems in which a carbocyclic, alicyclic, aromatic ring or heteroaryl ring is fused to one or more other heteroaryl or aryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl and 3-isoindolyl.

Suitable substituents for alkyl and aryl groups include —OH, halogen (—Br, —Cl, —I and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH, —S(R'), guanidine, alkyl, and aryl. Each R' is, independently, an alkyl group or an aromatic group. A substituted alkyl or aryl group can have more than one substituent.

Also included in the present invention are salts of the disclosed carboxylic acids. For example, amino acids can also be present in the anionic, or conjugate base, form, in combination with a cation. Suitable cations include alkali metal ions, such as sodium and potassium ions; alkaline earth ions, such as calcium and magnesium ions; and unsubstituted and substituted (primary, secondary, tertiary and quaternary) ammonium ions. Suitable cations also include transition metal ions such as manganese, copper, nickel, iron, cobalt, and zinc. Basic groups such as amines can also be protonated with a counter anion, such as hydroxide, halogens (chloride, bromide, and iodide), acetate, formate, citrate, ascorbate, sulfate or phosphate.

Alternative methods for synthesizing 2-alkylcysteines are described in co-pending U.S. Patent Application No. 60/380, 895, filed May 15, 2002, the entire contents of which are incorporated herein by reference.

EXEMPLIFICATION

Example 1

All compounds were used without further purification. The surfactants Rhodafac RE 610 and Soprophor FL were obtained from Rhône-Poulenc, Surfynol 465 from Air Products, Synperonic NP 10 from ICI and sodium lauryl sulfate from Fluka. For agitation a shaking machine was used (Buhler KL Tuttlingen). Purities of the resulting crystals were measured by using a PolarMonitor polarimeter (IBZ Hannover). Ethanol was used as the solvent. The total crystal quantity was dissolved in a 1 mL cell at 20 ° C.).

45 mg of (R,R)—and (S,S)-amino acid derivatives were dissolved in 1 ml of a mixture of 20% v/v 2-hexanol, 12% v/v Rhodafac RE 610, 6% v/v Soprophor FL and 62% v/v water by heating to 80° C. in a 5 mL vial. After the organic derivative was completely dissolved the microemulsion was cooled down to room temperature and agitated using a shaking machine (420 rpm). During two hours no spontaneous crystallization was observed. The mixture was then seeded with two drops of a dilute, finely ground suspension of pure (S,S)-(−) amino acid or its ester crystals grown under similar conditions. After 2 hours of agitation the resulting crystals were filtered off, washed with water and dried in a gentle nitrogen stream.

Example 2

35 mg of R- and S-4,5-dihydro-2-(2,4-dihydroxyphenyl)-4-methylthiazole-4-carboxylic acid were dissolved in 1 ml of a mixture of 9% N-methyl-pyrrolidone, 9% v/v 2-hexanol, 10% v/v Rhodafac RE 610, 5% v/v Soprophor FL and 68% v/v water by heating to 50° C. in a 5 mL vial. After the product was completely dissolved, the microemulsion was cooled down to room temperature and agitated with a shaking machine (350 rpm). During two hours, no spontaneous crystallisation was observed. The mixture was then seeded with two drops of a dilute, finely ground suspension of pure S-product crystals grown under similar conditions. After two hours of shaking, the resulting crystals were filtered off, washed with water and dried in a gentle nitrogen stream. The procedure yielded 5.4 mg (15.4%) of colorless crystals, with a greater than 90% purity of the S enantiomer.

Example 3

4.00 g (S)-2-methylcysteine hydrochloride (23.3 mmol, 1.0 meq) and 3.14 g 2,4-dihydroxy benzonitrile (23.3 mmol, 1.0 meq) were suspended in 40 mL ethanol. After degassing this mixture with nitrogen (30 min) 4.95 g triethylamine (6.8 mL, 48.9 mmol, 2.05 meq) were added. The obtained suspension was heated under reflux in an atmosphere of nitrogen for 20 hours and then cooled to room temperature. From this suspension ethanol was evaporated under reduced pressure until an oil (20% of the initial volume) was obtained. This oil was dissolved in 50 mL water. The solution was adjusted to pH 7.5 with 1.20 ml 20% KOH and was extracted two times each with 20 mL methyl t-butyl ether (MTBE). The aqueous layer was separated, adjusted with 20% KOH to pH 11 and again extracted two times each with 20 mL MTBE. After separating the aqueous layer the pH was set with concentrated HCl to 7.5 and traces of MTBE were distilled off. Then the aqueous solution was acidified with 1.50 ml concentrated HCl to pH 1.5. The product precipitated. This suspension was stirred at 4° C. for 1 hour. Then the precipitate was filtered, washed two times each with 10 mL water (5° C.) and dried at 45° C. under vacuum. The reaction yielded 5.17 g (87.6%) of crude 4,5-dihydro-2-(2,4-dihydroxyphenyl)-4-methylthiazole-4 (S)-carboxylic acid product. $^1$H-NMR showed no significant impurity.

Example 4

A single-neck 500 mL round-bottomed flask was flushed with nitrogen. (R)-(+)-L-cysteine hydrochloride monohydrate (12.0 g, 68.32 mmol) was transferred to the flask. Ethanol (240 mL) was added to give a suspension. Anhydrous triethylamine (34.6 g, 47.7 mL, 341.6 mmol, 5.0 equiv.) was then added via a syringe over a period of 10 min. at room temperature. A white precipitate of triethylamine hydrochloride formed immediately. After stirring this thick white turbid solution for 30 min. at room temperature, benzonitrile (7.05 g, 68.32 mmol) was added and the reaction mixture was refluxed for 6 hours. TLC ($CH_2Cl_2$ as eluent) indicated that all benzonitrile was consumed. The reaction mixture was cooled to room temperature and the solvent was removed in vacuo. Water (25 mL) was added followed by the addition of solid KOH (5 g) with stirring. This reddish clear aqueous solution (pH~11–12) was extracted with ethyl acetate (3×100 mL) and the organic layer was discarded. The aqueous layer was acidified with dropwise addition of 6M HCl to pH 1.5–2.0 to obtain an off-white to tan colored precipitate. This solid was filtered through a Buchner funnel. After drying under high vacuum, the solid was triturated with ethyl acetate to remove any traces of colored impurities. After filtration and drying, the off-white to white solid was stirred over dichloromethane to remove any traces of triethylamine hydrochloride and then filtered. After drying under vacuum, a white powdery solid was obtained (10.49 g, 74%).

Example 5

2,4-Dibenzyloxybenzonitrile (0.121 mol) was dissolved in 5.85 g (0.127 mol) ethanol and 19.4 ml 1,2-dimethoxyethane in a double walled reactor. This solution was cooled to −5° C., stirred and saturated with dry HCl gas over 5 hours at 0–3° C. The reaction mixture was stirred overnight at 2–4° C. under nitrogen. During this time, a product crystallized. The white crystals were filtered off, washed with 1,2-dimethoxyethane (5° C., three times each with 13 ml) and dried. A total of 30 of the protected ethyl benzimidate was isolated (Yield 88.4%, purity 98.9%).

The protected ethyl benzimidate described above was dissolved in methanol to generate a 10% solution and was catalytically hydrogenated at room temperature using 5% Pd/C as a catalyst. The reaction was completed after 8 hours. The solution was filtered and the solvent evaporated to yield the deprotected product as an orange-yellow solid. The reaction yielded 19.6 g (94%) of product.

In contrast, the formation of the imidate with 2,4 dihydroxybenzonitrile was a low yielding process, generating the desired product in only 20% yield and with less than desired purity.

While this invention has been particularly shown and described with references to preferred embodiments thereof, it will be understood by those skilled in the art that various changes in form and details may be made therein without departing from the scope of the invention encompassed by the appended claims.

We claim:

1. A method of preparing an optically active 2-alkylated cysteine represented by Structural Formula (I):

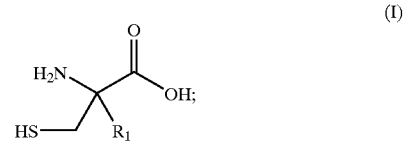

or a salt thereof;

wherein $R_1$ is a substituted or unsubstituted alkyl group, the method comprising:

(a) coupling a compound represented by Structural Formula (II):

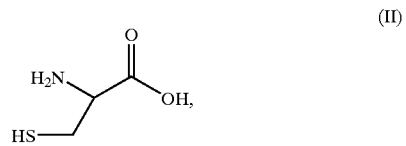

or a salt thereof, with a substituted or unsubstituted aryl nitrile of the formula Ar—CN, wherein Ar is a substituted or unsubstituted aryl group; thereby forming a substituted thiazoline carboxylic acid represented by Structural Formula (III):

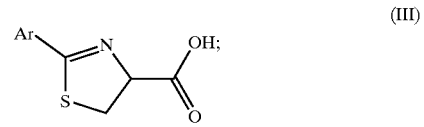

(b) esterifying the substituted thiazoline carboxylic acid with R*—OH, wherein R* is a substituted or unsubstituted alkyl group comprising one or more chiral carbon atoms; thereby forming a substituted thiazoline carboxylic acid ester represented by Structural Formula (IV):

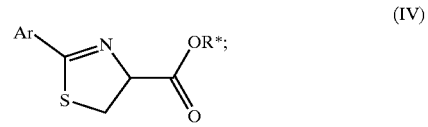

(c) alkylating the substituted thiazoline carboxylic acid ester with one or more bases and $R_1X$, wherein X is a leaving group and $R_1$ is as defined above; thereby forming an alkylated substituted thiazoline carboxylic acid ester represented by Structural Formula (V):

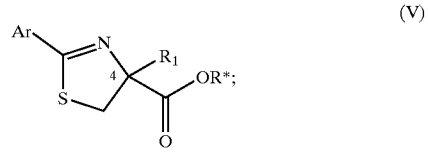

(d) hydrolyzing the alkylated substituted thiazoline carboxylic acid ester with base or acid, thereby forming an alkylated substituted thiazoline carboxylic acid represented by Structural Formula (VI):

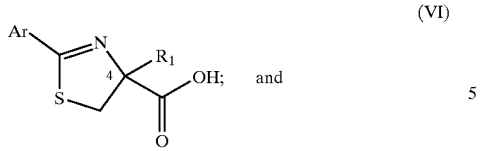

(e) reacting the alkylated substituted thiazoline carboxylic acid with acid, thereby forming the 2-alkylated cysteine represented by Structural Formula (I).

2. The method of claim 1, wherein Ar is a substituted or unsubstituted phenyl group.

3. The method of claim 2, wherein Ar is phenyl.

4. The method of claim 1, wherein R*—OH is selected from the group consisting of (1R,2R,3R,5S)-(−)-isopinocamphenol and (1S,2R,5R)-(+)-isomenthol.

5. The method of claim 1, wherein the one or more bases of step (c) are selected from the group consisting of potassium t-butoxide, sodium methoxide, sodium ethoxide, and sodium amide.

6. The method of claim 1, wherein $R_1$ is a substituted or unsubstituted C1–C4 alkyl group.

7. The method of claim 6, wherein $R_1$ is methyl.

8. The method of claim 1, wherein X is iodine.

9. The method of claim 1, further comprising the step of purifying the alkylated substituted thiazoline carboxylic acid ester by resolving the enantiomers of the alkylated substituted thiazoline carboxylic acid ester.

10. The method of claim 9, wherein the (S)-isomer, based on carbon atom 4 as indicated in Structural Formula (V), of the alkylated substituted thiazoline carboxylic acid ester is isolated from the enantiomers of the alkylated substituted thiazoline carboxylic acid ester.

11. The method of claim 1 further comprising the step of purifying the alkylated substituted thiazoline carboxylic acid by resolving the enantiomers of the alkylated substituted thiazoline carboxylic acid.

12. The method of claim 11, wherein the (S)-isomer of the alkylated substituted thiazoline carboxylic acid is isolated from the enantiomers of the alkylated substituted thiazoline carboxylic acid.

13. A method of preparing a compound represented by Structural Formula (II):

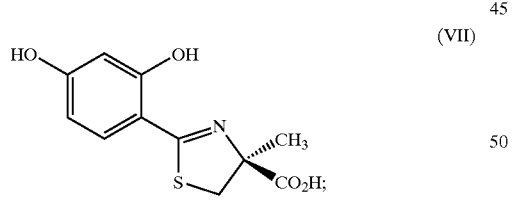

or a salt thereof, the method comprising:
(a) coupling a compound represented by Structural Formula (VIII):

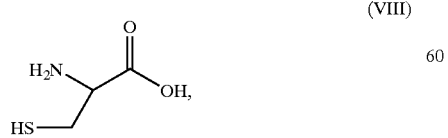

or a salt thereof, with a substituted or unsubstituted aryl nitrile of the formula Ar—CN, wherein Ar is a substituted or unsubstituted aryl group; thereby forming a substituted thiazoline carboxylic acid represented by Structural Formula (IX):

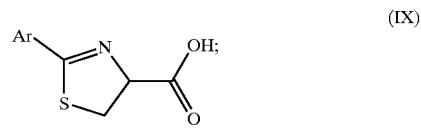

(b) esterifying the substituted thiazoline carboxylic acid with R*—OH, wherein R* is a substituted or unsubstituted alkyl group comprising one or more chiral carbon atoms; thereby forming a substituted thiazoline carboxylic acid ester represented by Structural Formula (X):

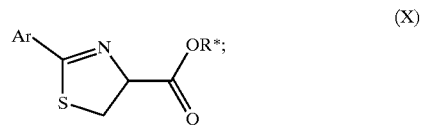

(c) alkylating the substituted thiazoline carboxylic acid ester with one or more bases and $CH_3X$, wherein X is a leaving group; thereby forming an alkylated substituted thiazoline carboxylic acid ester represented by Structural Formula (XI):

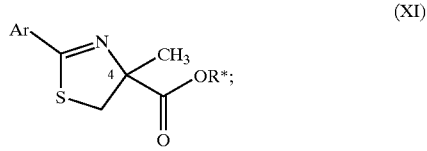

(d) hydrolyzing the alkylated substituted thiazoline carboxylic acid ester with base or acid, thereby forming an alkylated substituted thiazoline carboxylic acid represented by Structural Formula (XII):

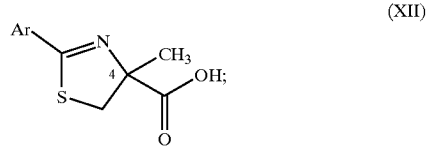

(e) optionally, purifying the (S)-isomer of the alkylated substituted thiazoline carboxylic acid;

(f) reacting the (S)-isomer of the alkylated substituted thiazoline carboxylic acid with acid, thereby forming (S)-2-methylcysteine; and (g) coupling (S)-2-methylcysteine with 2,4-dihydroxybenzonitrile, thereby forming the compound represented by Structural Formula (VII).

* * * * *

UNITED STATES PATENT AND TRADEMARK OFFICE
CERTIFICATE OF CORRECTION

PATENT NO. : 6,878,828 B2
DATED : April 12, 2005
INVENTOR(S) : Rayomand H. Gimi, Mukund S. Chorghade and Sunil V. Mhaskar It is certified that error appears in the above-identified patent and that said Letters Patent is hereby corrected as shown below:

Column 13,
Line 44, "(II)" should be -- VII --.

Signed and Sealed this

Twenty-eighth Day of June, 2005

JON W. DUDAS
*Director of the United States Patent and Trademark Office*